United States Patent [19]
Gielen et al.

[11] Patent Number: 5,559,147
[45] Date of Patent: Sep. 24, 1996

[54] AROMATIC FLUORINE-CONTAINING ORGANOTIN COMPOUNDS AND ANTI-TUMOUR COMPOSITION

[75] Inventors: Marcel Gielen, Wezenbeek-Oppem; Rudolph Willem, Vilvoorde; Abdeslam Bouhdid, Brussel, all of Belgium; Dick de Vos, Oegstugeest, Netherlands

[73] Assignee: Pharmachemie B.V., Haarlem, Netherlands

[21] Appl. No.: 519,026

[22] Filed: Aug. 24, 1995

[30] Foreign Application Priority Data

Sep. 9, 1994 [EP] European Pat. Off. .............. 94202612

[51] Int. Cl.$^6$ ................................ A61K 31/32; C07F 7/22
[52] U.S. Cl. .............................. 514/493; 556/82; 556/90; 556/92; 556/94; 556/105
[58] Field of Search .................................. 556/82, 90, 92, 556/94, 105; 514/493

[56] References Cited

FOREIGN PATENT DOCUMENTS

0472783A1  3/1992  European Pat. Off. .

OTHER PUBLICATIONS

Moens et al, "Fungicidal Activity of a Series of Tri–and Diorganotin Compounds", Chemical Abstracts, Abstract No. 24470e, 1993.

Deacon et al, "Decarboxylation Syntheses of Some Polyfluo= Rophenyltin and—Germanium Compounds," Chemical Abstracts, Abstract No. 201657q, 1977.

Gielen et al, "Diorganotin Diflurobenzoates: Synthesis, Spec= Troacopic Characterization and In Vitro Antitumor Activity", Chemical Abstracts, Abstract No. 245345r, 1993.

*Primary Examiner*—Porfirio Nazario-Gonzales
*Attorney, Agent, or Firm*—Browdy and Neimark

[57] ABSTRACT

The invention relates to novel aromatic fluorine-containing organotin compounds of the formula $\{(F_5C_6RCO_2SnBu_2)_2O\}_2$ and $\{(F_5C_6RCO_2)_2SnBu_2\}$ wherein R is $CH_2$, $CH=CH$ or a single bond between the phenyl ring and the $CO_2$ group, and Bu is a butyl group; as well as to anti-tumour compositions containing as an active ingredient one or more of these compounds.

3 Claims, No Drawings

AROMATIC FLUORINE-CONTAINING ORGANOTIN COMPOUNDS AND ANTI-TUMOUR COMPOSITION

This invention relates to novel aromatic fluorine-containing organotin compounds and to anti-tumour compositions containing said compounds.

DISCLOSURE OF THE PRIOR ART

The substitution of hydrogen for fluorine substantially influences the biological activity of organic molecules (J. T. Welch, *Tetrahedron*, 43 (1987), 3123).

Fluorine (Van der Waals radius: 1.35 Å) resembles hydrogen (Van der Waals radius: 1.20 Å) but, because of the strength of the C-F bond, the fluorine substituent is very resistant to metabolic transformations. The very high electronegativity of fluorine, however, makes it quite different from hydrogen: its presence strongly affects the electronic distribution in the molecule, i.e. its dipole moment, the basicity, acidity or reactivity of neighbouring groups, etc.

We have already synthesized several fluorine-containing organotin compounds, of which the antitumour activity was screened against two human tumour cell lines, MCF-7, a mammary tumour, and WiDR, a colon carcinoma.

The di-n-butyltin monofluorobenzoates $\{(4\text{-F-C}_6H_4CO_2SnBu_2)_2O\}_2$ and $(4\text{-F-}C_6H_4CO_2)_2 SnBu_2$ (see M. Gielen, A. El Khloufi, M. Biesemans and R. Willem, *Appl. Organomet. Chem.*, 7 (1933), 119–125) are characterized by $ID_{50}$ values of 81 and 360, and 90 and 309 ng/ml, respectively, comparable to those observed for etoposide. Of the corresponding difluorobenzoates (see M. Gielen, M. Biesemans, A. El Khloufi, J. Meunier-Piret, F. Kayser and R. Willem, *J. Fluorine Chem.*, 64 (1993), 279–291), the 2,3-difluorobenzoates $\{(2,3\text{-F}_2C_6H_3CO_2SnBu_2)_2O\}_2$ and $(2,3\text{-}F_2C_6H_3CO_2)_2SnBu_2$, exhibit for instance $ID_{50}$ values of 9 and 120, and 23 and 283 ng/ml, respectively. This clearly shows that, at least against MCF-7, the activity is enhanced when the number of fluorine atoms of the benzoate moiety is increased. These activities are comparable to mitomycin C. The $ID_{50}$ values of corresponding tri- and tetrafluorobenzoates, $\{(2,3,6\text{-F}_3C_6H_3CO_2SnBu_2)_2O\}_2$ and $\{(2,3,4,5\text{-}F_4C_6HCO_2 SnBu_2)_2O\}_2$, are of the same order of magnitude: 13 and 200, and 35 and 250 ng/ml, respectively (see M. Gielen, A. El Khloufi, D. de Vos, H. J. Kolker, J. H. M. Schellens and R. Willem, *Bull. Soc. Chim. Belg.*, 102 (1993), 761–764).

Di-n-butyltintetrafluorophthalate, $F_4C_6\text{-}1,2\text{-}(CO_2)_2SnB_2$, (see M. Gielen, M. Bouâlam, A. Meriem, B. Mahieu, M. Biesemans and R. Willem, Heteroatom Chem., 3 (1992), 449–452) is characterized by very low $ID_{50}$ values, especially against WiDr, viz. 51 and 68 ng/ml.

The di-n-butyltin 2-fluorocinnamates and 4-fluorophenylacetates, $\{(2\text{-F-}C_6H_4CH=CHC_2SnBu_2)_2O\}_2$ and $\{(4\text{-F-}C_6H_4CH_2CO_2SnBu_2)_2O\}_2$ (see M. Gielen, A. El Khloufi, M. Biesemans, F. Kayser and R. Willera, *Appl. Organomet. Chem.*, 7 (1993), 201–206) have comparable activities, i.e. $ID_{50}$ values of 28 and 368, and 38 and 268 ng/ml.

SUMMARY OF THE INVENTION

The present invention provides novel aromatic fluorine-containing organotin compounds of the formula $\{(F_5C_6RCO_2SnBu_2)_2O\}_2$ or $\{(F_5C_6RCO_2SnBu_2)\}$ wherein R is $CH_2$, $CH=CH$ or a single bond between the phenyl ring and the $CO_2$ group, and Bu is a butyl group.

This invention also provides anti-tumour compositions, containing as an active ingredient one or more aromatic fluorine-containing organotin compounds as defined above, and a pharmaceutically acceptable carrier.

The present compounds show a markedly better solubility in polar solvents, such as ethanol, than the above discussed tested compounds; the solubility of the present compounds in ethanol is about 10 times higher than that of the known compounds (about 50 mg/ml). Furthermore, the present compounds show activities against a broad spectrum of tumours, as appears from the experimental part disclosed hereinafter.

DESCRIPTION OF THE PREFERRED EMBODIMENTS

Syntheses and purifications

The compounds 1 to 3 of the general formula $\{F_5C_6CO_2SnBu_2)_2O\}_2$, $\{(F_5C_6CH_2CO_2SnBu_2)_2O\}_2$ and $\{(F_5C_6CH=CHCO_2SnBu_2)_2O\}_2$, were synthesized from the corresponding organic acid and di-n-butyltin oxide in a 1:1 molar ratio, and $\{(F_5C_6CH_2CO_2)_2SnBu_2\}$, 4, was synthesized employing a 2:1 molar ratio, using the following procedure: The appropriate acid was dissolved in a 4:1 mixture of toluene and ethanol. The reacting mixture was refluxed for 4 to 6 h. The ternary azeotrope, water/ethanol/toluene, followed by the binary, azeotrope ethanol/toluene, were distilled off with a Dean-Stark funnel up to 50% reduction of the initial volume. The solvents were evaporated under reduced pressure. The solid or oil obtained was purified by recrystallization in appropriate solvents.

The following compounds were prepared:

$\{(F_5C_6CO_2SnBu_2)_2O\}_2$, compound 1

Recrystallized from ethanol/petroleum ether; mp: 151°–153° C., yield: 94%; Mössbauer parameters (in mm/s): QS: 3.68, IS: 1.42, $\Gamma_1$ & $\Gamma_2$:1.10 & 0.98; $^1$H NMR (CDCl$_3$): α& β-CH$_2$: m, 1.46–1.78; γ-CH$_2$; tq, 1.34 [7, 7] and tq: 1,51 [7,7]; CH$_3$;t, 0.87 [7] and t: 0.89 [7]; $^{13}$C NMR (CDCl$_3$): C-1: td, 111.8 [4, 19]; C-2 & C-6: bd, 141.8 [253]; C-3 & C-5: bd, 137.8 [248]; C-4: bd, 144.2 [264]; CO; 164.3; α-C: 28.7 [bs] and 29.8 [bs]; β-C: 27.0 [$^2$J($^{13}$C-$^{119/117}$Sn): 35] and 27.3 [$^2$J($^{13}$C-$^{119/117}$Sn): 35]; γ-C: 26.6 [$^3$J($^{13}$C-$^{119/117}$Sn): 121] and 26.7 [$^3$J($^{13}$C-$^{119/117}$Sn): 123]; CH$_3$13.2 and 13.3; $^{19}$F NMR (CFCl$_3$): F-2 & F-6: dddd,–141.4 [$^n$J($^{19}$F—$^{19}$F): 21, 3, 2,–8]; F-3 & F-5: dddd, –161.2 [$^n$J($^{19}$F—$^{19}$F): 21, 21, 3,–8]; F-4: t, –152.1 [$^3$J($^{19}$F—$^{19}$F): 21]; $^{119}$Sn NMR (CDCl$_3$):–189,5,–190.6 [$^2$ J($^{119}$Sn-O-$^{117/119}$Sn): 126]

$\{(F_5C_6CH_2CO_2SnBu_2)_2O\}_2$, compound 2

Recrystallized from ethanol/petroleum ether; mp: 76°–77° C., yield; 85%; Mössbauer parameters (in mm/s): QS: 3.39, IS: 1.29, $\Gamma_1$ & $\Gamma_2$: 0.96 & 0.99; $^1$H NMR (CDCl$_3$): CH$_2$CO: S, 3.56; α- & β-CH$_2$: m, 1.44–1.54; γ-CH$_2$; tq 1.27 [7, 7] and tq: 1,29 [7,7]; CH$_3$: t, 0.86 [7] and t: 0.89 [7]; $^{13}$C NMR (CDCl$_3$): C-1; dt, 109.9 [17, 4]; C-2 & C-6: bd: 145.3 [247]; C-3 & C-5: bd: 137.4 [253]; C-4; bd; 140.3 [249]; CH$_2$CO: 29.6; CO: 173.9; α-C: 29.5 [bs] and 29.1 [bs]; β-C: 27.2 [$^2$J($^{13}$C-$^{119/117}$Sn): 32] and 27.6 [$^2$J($^{13}$C-$^{119/117}$Sn): 37]; γ-C: 26.6 [$^3$J($^{13}$C- $^{119/117}$Sn): 125] and 26.8 [b]; CH$_3$: 13.2 and 13.3; $^9$F NMR (CFCl$_3$): F-2 & F-6: dddd,–143.4 [$^n$J($^{19}$F—$^{19}$F): 21, 3, 2,–9]; F-3 & F-5: bs ,–163.3; F-4: bs,–156.8; $^{119}$Sn NMR (CDCl$_3$):–204.6,–209.3 [$^2$J($^{119}$Sn-O-$^{117/119}$Sn): 121]

$\{(F_5C_6CH=CHCO_2SnBu_2)_2O\}_2$, compound 3

Recrystallized from ethanol/petroleum ether; mp: 110°–112° C., yield: 93%; Mössbauer parameters (in mm/s): QS: 3.53, IS: 1.34, $\Gamma_1$ & $\Gamma_2$: 0.98 & 0.99; $^1$H NMR (CDCl$_3$): α-CH: d, 6.70 [16]; β-CH: d, 7.52 [16]; α- & β-CH$_2$: m; 1.64–1.75; γ-CH$_2$: tq, 1.37 [7, 7] and tq: 1,43 [7,7]; CH$_3$: t, 0.86 [7] and t: 0.89 [7]; $^{13}$C NMR (CDCl$_3$): C-1: td, 110.4

[4, 14]; C-2 & C-6: bd: 145.5 [254]; C-3 & C-5: 137.5 [249]; C-4: bd: 1:37.9 [249]; α-CH: 130.0; β-CH: 126.9; CO: 171.4; α-$CH_2$: 29.7 [bs] and 29.7 [bs]; β-$CH_2$: 27.4 [$^2J(^{13}C$-$^{119/117}Sn$): 36] and 27.7 [$^2J(^{13}C$-$^{119/117}Sn$); 36]; γ-$CH_2$: 26.6 [$^3J(^{13}C$-$^{119/117}Sn$): 121] and 26.8 [$^3J(^{13}C$-$^{119/117}Sn$); 125]; $CH_3$: 13.2 and 13.3; $^{19}F$ NMR ($CFCl_3$): F-2 & F-6: dddd,–140.4 [$^n J(^{19}$-F— $^{19}F$): 21,3, 1, –8]; F-3 & F-5: dddd,–162.7 [21, 21,3,–8]; F-4: t,–152.9 [21]; $^{119}Sn$ NMR ($CDCl_3$): –206.6, –215.5 [$^2J(^{119}Sn$-O-$^{117/119}Sn$): 113] $\{(F_5C_6CH_2CO_2)_2SnBu_2\}$, compound 4

Recrystallized from ethanol/hexane; mp: 125°–126° C., yield: 90%; Mössbauer parameters (in mm/s): QS: 3.85, IS: 1.51, $\Gamma_1$ & $\Gamma_2$: 0.99 & 0.89; $^1H$ NMR ($CDCl_3$): $CH_2CO$: s, 3.70; α- & β-$CH_2$; m, 0.58–1.72; γ-$CH_2$; tq, 1.34 [7, 7]; $CH_3$; t, 0.88 [7]; $^{13}C$ NMR ($CDCl_3$): C-1: td, 108.7 [3, 18]; C-2 & C-6: bd: 145.3 [248]; C-3 & C-5: bd: 137.5 [253]; C-4: bd: 140.6 [253]; $CH_2CO$: 27.7; CO: 178.1; α-C; 25.6 [$^1J(^{13}C$-$^{119/1117}Sn$): 561/536]; β-C: 26.4 [$^2J(^{13}C$-$^{119/117}Sn$): 35]; γ-C; 26.2 [$^3J(^{13}C$-$^{119/117}Sn$): 95]; $CH_3$: 13.3; $^{19}F$ NMR ($CFCl_3$): F-2 & F-6: dddd, –143.1 [$^nJ(^{19}F$—$^{19}F$): 21, 3, 1,–8]; F-3 & F-5: dddd,–162.9 [21, 21, 3,–8]; F-4: t, –156.1 [21]; $^{119}Sn$ NMR ($CDCl_3$):–131.3

The above compounds were tested in vitro against the following human tumour cell lines
MCF-7 breast cancer
EVSA-T breast cancer
WIDR colon cancer
IGROV ovarian cancer
M19 MEL melanoma
A498 renal cancer The tests were carried out according to the method of Y. P. Kepers, P. E. Pizao, G. J. Peters, J. Van Ark-Otte, B. Winograd, H. M. Pinedo, Comparison of the sulforhodamine B protein and tetrazolium (MTT) assays for in vitro chemosensitivity testing. Eur. J. Cancer 27: 897–900; 1991.

The $ID_{50}$ values in mg/ml for the above for compounds and for two known compounds (carboplatin and cisplatin) were determined according to the above mentioned procedure. $ID_{50}$ is the amount which inhibits 50% of the cell growth. The results are shown in the following table.

| | $ID_{50}$ values in mg/ml | | | | | |
|---|---|---|---|---|---|---|
| Compounds | MCF-7 | EVSAT | WiDr | IGROV | M19 | A498 |
| 1 | 44 | 39 | 214 | 53 | 86 | 76 |
| 2 | 55 | 43 | 275 | 60 | 114 | 105 |
| 3 | 32 | 37 | 234 | 41 | 66 | 135 |
| 4 | 10 | 19 | 145 | 20 | 36 | 51 |
| Carboplatin | 5500 | 1100 | 1500 | 780 | 5300 | 3500 |
| Cisplatin | 800 | 1200 | 650 | 79 | 530 | 1200 |

From the above results it can be seen that the present organotin compounds exhibit excellent $ID_{50}$ values which are considerably lower than the $ID_{50}$ values of the known compounds which were tested for comparative purposes.

What is claimed is:

1. An aromatic fluorine-containing organotin compound of the formula $\{(F_5C_6RCO_2SnBu_2)_2O\}_2$ or $\{(F_5C_6RCO_2)_2SnBu_2\}$ wherein R is $CH_2$, CH=CH or a single bond between the phenyl ring and the $CO_2$ group, and Bu is a butyl group.

2. An anti-tumour composition, containing as an active ingredient one or more aromatic fluorine-containing organotin compounds of the formula $\{(F_5C_6RCO_2SnBu_2)_2O\}_2$ or $\{(F_5C_6RCO_2)_2SnBu_2\}$ wherein R and Bu have the meanings defined in claim 1, and a pharmaceutically acceptable carrier.

3. A process of preparing an aromatic fluorine-containing organotin compound of the formula $\{(F_5C_6RCO_2SnBu_2)_2O\}_2$ or $\{(F_5C_6RCO_2)_2SnBu_2\}$ wherein R is $CH_2$, CH=CH or a single bond between the phenyl ring and the $CO_2$ group, and Bu is a butyl group, by reacting the corresponding acid with di-n-butyltin in a molar ratio of from 1:1 to about 2:1 under reflux conditions in a suitable solvent, followed by removal of the solvent to obtain the desired compound.

* * * * *